(12) United States Patent
Green et al.

(10) Patent No.: US 6,679,888 B2
(45) Date of Patent: Jan. 20, 2004

(54) FEMUR LEVER

(75) Inventors: James M. Green, Portland, OR (US); Stanley J. Kmiec, Jr., Morgantown, PA (US)

(73) Assignee: Synthes, Paoli, PA (US)

( * ) Notice: Subject to any disclaimer, the term of this patent is extended or adjusted under 35 U.S.C. 154(b) by 0 days.

(21) Appl. No.: 09/865,507

(22) Filed: May 29, 2001

(65) Prior Publication Data

US 2002/0183759 A1 Dec. 5, 2002

(51) Int. Cl.$^7$ .................................................. A61F 5/00
(52) U.S. Cl. ........................................... 606/86; 606/96
(58) Field of Search ...................... 606/86, 96, 105, 606/107, 88, 87, 70, 69, 71, 72, 205, 206, 207, 208

(56) References Cited

U.S. PATENT DOCUMENTS

| | | | | |
|---|---|---|---|---|
| 1,217,637 A | * | 2/1917 | Rink ............................ 606/76 |
| 1,346,940 A | * | 7/1920 | Collins ........................ 606/103 |
| 2,112,447 A | | 3/1938 | Peterson ...................... 128/83 |
| 3,477,429 A | * | 11/1969 | Sampson ..................... 606/86 |
| 3,867,932 A | | 2/1975 | Huene .......................... 128/92 |
| 3,960,147 A | | 6/1976 | Murray ......................... 128/92 |
| 4,106,508 A | * | 8/1978 | Berlin ............................ 251/7 |
| 4,232,660 A | | 11/1980 | Coles ........................... 128/20 |
| 4,364,381 A | | 12/1982 | Sher et al. .................... 128/92 |
| 4,535,768 A | | 8/1985 | Hourahane et al. ......... 128/305 |
| 4,621,630 A | | 11/1986 | Kenna ........................... 128/92 |
| 4,642,121 A | | 2/1987 | Keller .......................... 623/18 |
| 4,686,972 A | | 8/1987 | Kurland ......................... 128/92 |
| 4,708,320 A | | 11/1987 | Hodges ........................ 254/129 |
| 4,781,182 A | * | 11/1988 | Purnell et al. ................ 606/86 |
| 4,787,377 A | | 11/1988 | Laboureau ..................... 128/92 |
| 4,813,407 A | * | 3/1989 | Vogen ......................... 606/151 |
| 4,955,885 A | | 9/1990 | Meyers ......................... 606/53 |
| 4,995,875 A | | 2/1991 | Coes ............................ 606/90 |
| 5,020,519 A | | 6/1991 | Hayes et al. .................. 128/69 |
| 5,026,376 A | | 6/1991 | Greenberg ..................... 606/96 |
| 5,133,342 A | | 7/1992 | Seaton ......................... 602/39 |
| 5,133,720 A | * | 7/1992 | Greenberg ..................... 606/86 |
| 5,163,940 A | | 11/1992 | Bourque ....................... 606/96 |
| 5,217,463 A | | 6/1993 | Mikhail ........................ 606/88 |
| 5,290,290 A | | 3/1994 | Mikhail ........................ 606/88 |
| 5,308,349 A | | 5/1994 | Mikhail ........................ 606/88 |
| 5,312,412 A | | 5/1994 | Whipple ....................... 606/96 |
| 5,380,331 A | | 1/1995 | Mikhail ........................ 606/79 |
| 5,391,169 A | | 2/1995 | McGuire ...................... 606/79 |

(List continued on next page.)

FOREIGN PATENT DOCUMENTS

| EP | 0 380 309 A1 | 8/1990 |
|---|---|---|
| EP | 0 645 992 B1 | 3/1998 |
| RU | 1718888 A1 | 3/1992 |

OTHER PUBLICATIONS

Orthopedic Technology Review, "On The Market", May 2000, p. 50.

* cited by examiner

Primary Examiner—Pedro Philogene
(74) Attorney, Agent, or Firm—Pennie & Edmonds LLP

(57) ABSTRACT

A lever for grasping bone tissue includes a shaft defining a channel and having a proximal end and a distal end, a claw member disposed on the distal end of the shaft for holding the bone tissue, and a rod threadably received in the channel and having a proximal end and a distal end. Rotation of the rod with respect to the shaft causes the rod to move substantially axially with respect to the shaft to selectively position the distal end of the rod with respect to the claw member. The lever may further include a locking member to allow the rod to slide axially with respect to the shaft. Various other features which improve the functioning of the lever may be provided separately or in combination.

42 Claims, 18 Drawing Sheets

U.S. PATENT DOCUMENTS

| | | |
|---|---|---|
| 5,431,653 A | 7/1995 | Callaway .................. 606/90 |
| 5,431,658 A | 7/1995 | Moskovich ................. 606/99 |
| 5,474,560 A | 12/1995 | Rohr, Jr. .................. 606/91 |
| 5,520,693 A | 5/1996 | McGuire et al. ............. 606/86 |
| 5,562,664 A | 10/1996 | Durlacher et al. ........... 606/96 |
| 5,578,032 A | 11/1996 | Lalonde .................... 606/54 |
| 5,584,839 A | 12/1996 | Gieringer .................. 606/96 |
| 5,601,550 A | 2/1997 | Esser ...................... 606/54 |
| 5,601,562 A | 2/1997 | Wolf et al. ................ 606/86 |
| 5,611,814 A | 3/1997 | Lorenc ..................... 606/213 |
| 5,613,971 A | 3/1997 | Lower et al. ............... 606/96 |
| 5,624,443 A | 4/1997 | Burke ...................... 606/86 |
| 5,624,446 A | 4/1997 | Harryman, II .............. 606/96 |
| 5,626,583 A | 5/1997 | Davis, Jr. .................. 606/72 |
| 5,649,929 A | 7/1997 | Callaway ................... 606/88 |
| 5,690,640 A | 11/1997 | Gotfried ................... 6065/105 |
| 5,700,266 A | 12/1997 | Harryman, II .............. 606/80 |
| 5,709,682 A | 1/1998 | Medoff ..................... 606/60 |
| 5,725,532 A | 3/1998 | Shoemaker ................. 606/96 |
| 5,733,289 A | 3/1998 | Seedhom et al. ............ 606/80 |
| 5,733,291 A | 3/1998 | Guidera et al. ............. 606/86 |
| 5,746,743 A * | 5/1998 | Greenberg ................. 600/210 |
| 5,827,288 A | 10/1998 | Umber et al. .............. 606/80 |
| 5,910,141 A | 6/1999 | Morrison et al. ............ 606/61 |
| 5,951,564 A | 9/1999 | Schroder et al. ............ 606/100 |
| 5,971,920 A | 10/1999 | Nagel ...................... 600/206 |
| 5,989,259 A | 11/1999 | Penenberg et al. .......... 606/99 |
| 6,022,357 A | 2/2000 | Reu et al. .................. 606/99 |

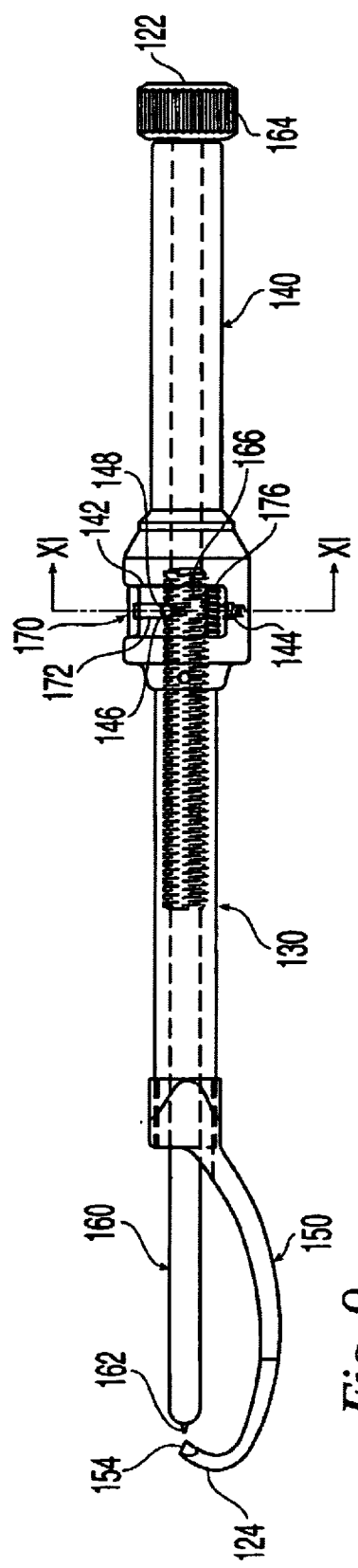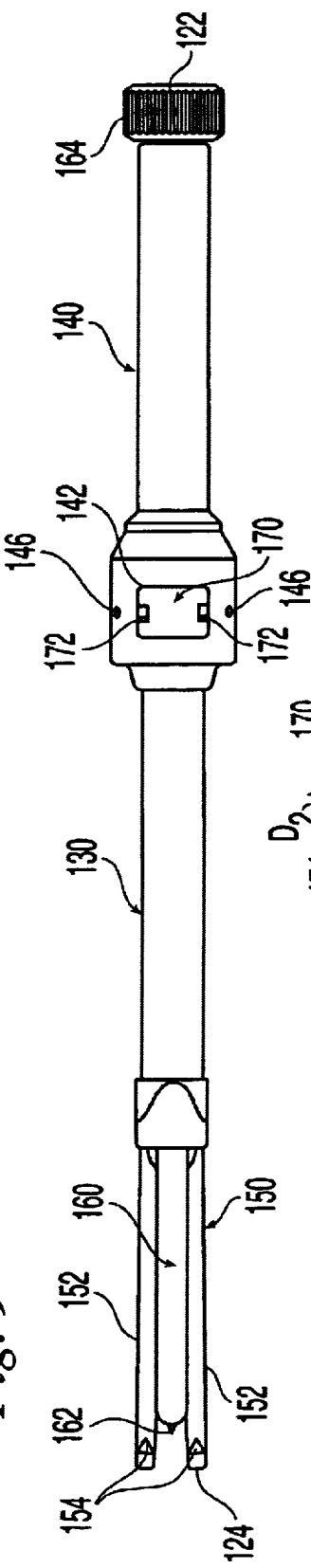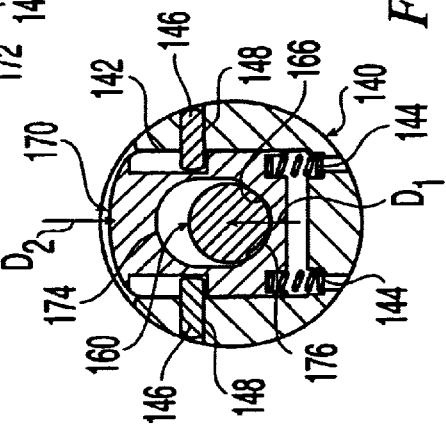

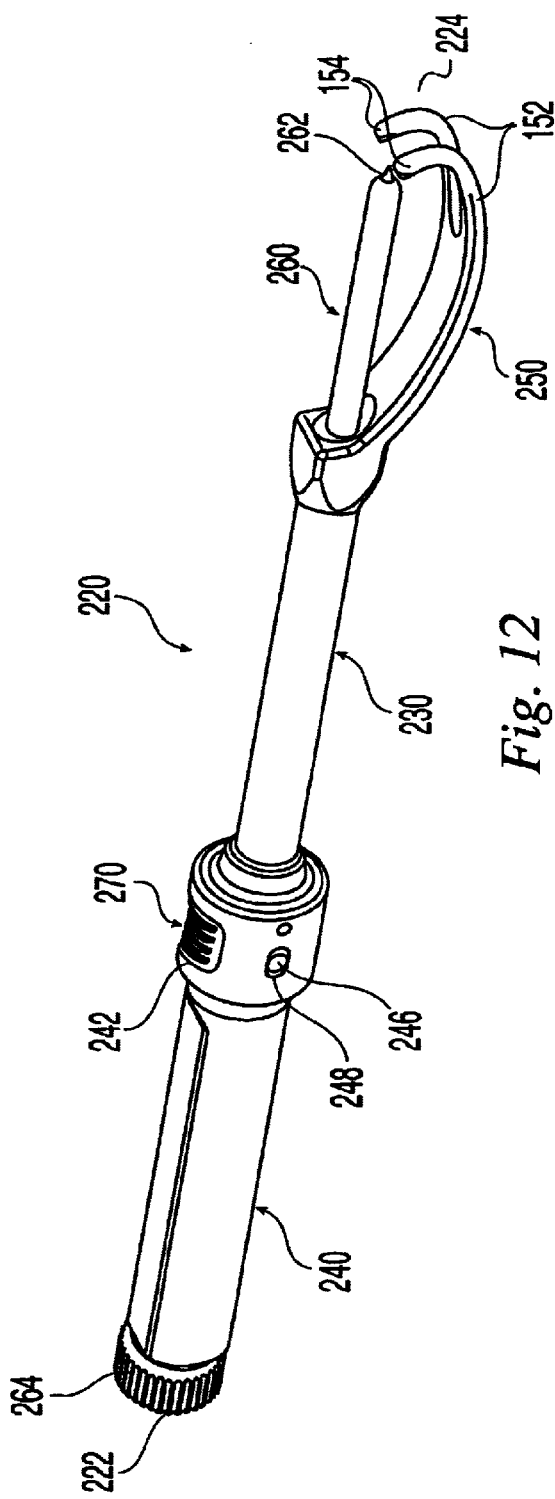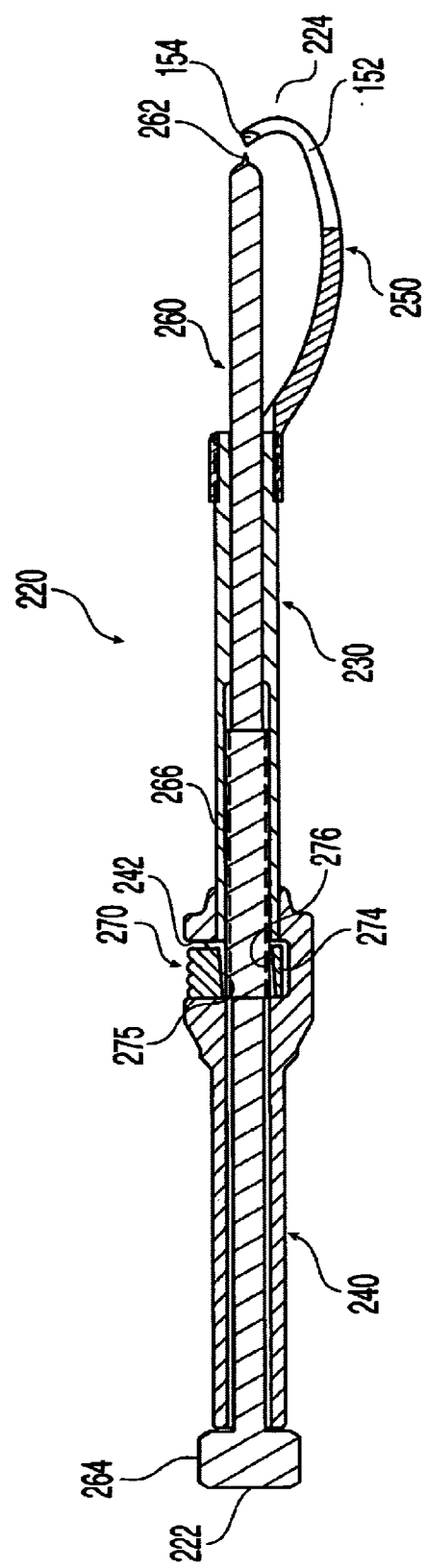

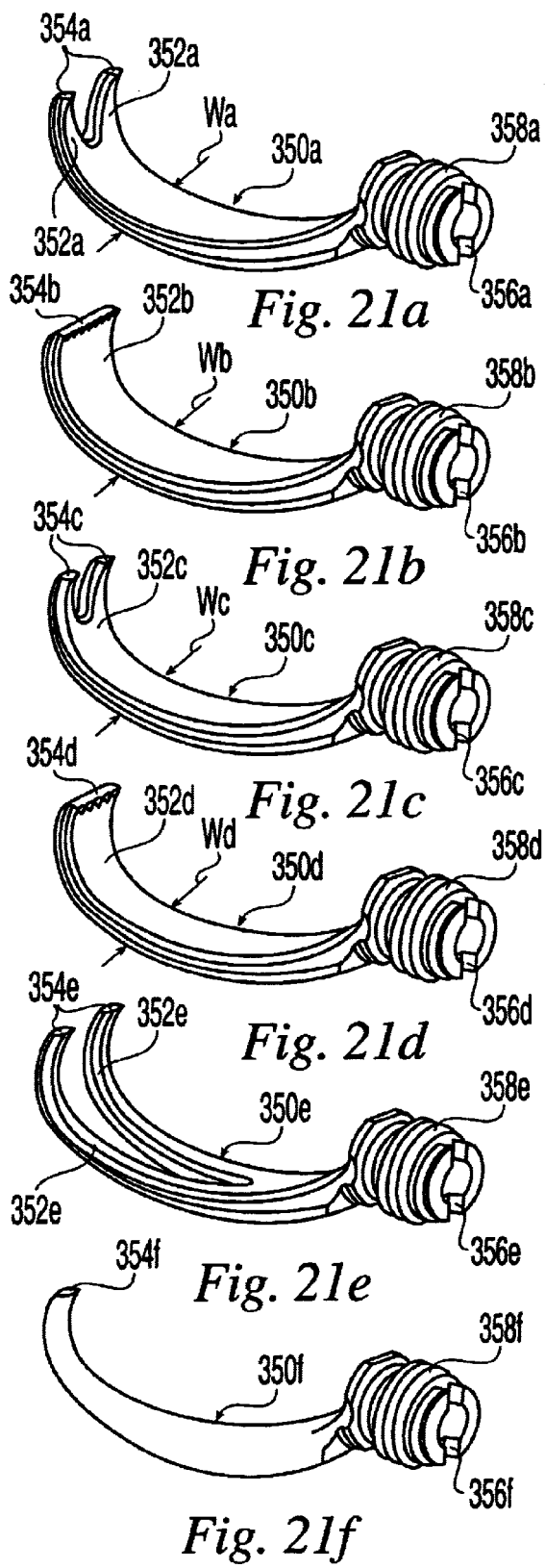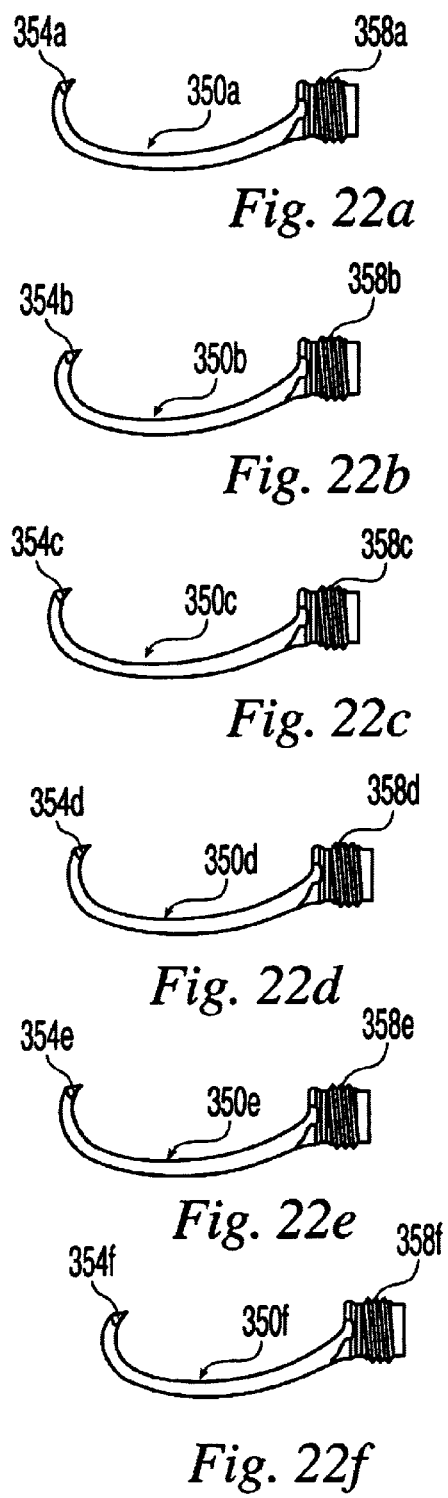

FEMUR LEVER

TECHNICAL FIELD OF THE INVENTION

The present invention relates to medical devices, and in particular, to medical devices for grasping and manipulating bones. More particularly, the present invention relates to a lever for grasping and manipulating the fragments of a fractured bone, including the proximal fragment of a fractured femur.

BACKGROUND OF THE INVENTION

Fractures of the proximal femoral shaft have proven difficult to manipulate in preparation for internal fixation. For example, when proximal shaft fractures of the femur occur, the distal end of the proximal fragment rotates anterior (flexion) and lateral (abduction) creating difficulty in accessing the piriformis fossa, the desired entry point for intramedullary nailing or other methods of internal fixation.

Several devices for aligning fractured bones are described in the prior art. For example, U.S. Pat. Nos. 5,133,342 to Seaton and 5,733,291 to Guidera et al. describe bone alignment levers that are applied to the exterior of the patient's leg and maneuvered to align portions of a fractured bone. These external devices, however, do not provide adequate manipulation of the bone to rotate fractured bone portions such as the proximal femoral shaft back into proper alignment.

Internal devices for aligning fractured bones are also described in the prior art. One example is U.S. Pat. No. 5,312,412 to Whipple, which describes a fixation alignment guide that includes an axially movable shaft having a bone engagement arm extending outwardly therefrom for engaging a fractured bone at a first surface location. A tubular guide through which the shaft is inserted includes jaws opposing the bone engagement arm for engaging the fractured bone at a second surface location. A ratchet mechanism and cooperating ratchet teeth are operatively associated with the guide for securing the bone engagement arm at a desired distance from the jaws to fixedly engage the fractured bone therebetween. The jaws and engagement arm are spaced apart laterally and define a large profile that requires a large incision for insertion into the patient. In addition, the ratchet mechanism and ratchet teeth only provide for incremental adjustment of the distance between the jaws and the engagement arm, and thus limit the user's ability to precisely adjust the amount of force applied to the bone.

Another fixation alignment guide is described in U.S. Pat. No. 5,690,640 to Gotfried. This device includes a first hook for gripping the rear surface of the bone and a screw-threaded bar and handle which extend to the outside of the limb. A second hook for gripping a connector plate is movable on the bar. The two hooks are pulled together by a winged nut screwed onto the bar, thereby pressing the plate onto the bone. Similar to the Whipple device, discussed above, the two hooks require a large incision for insertion into the patient. Also, the speed at which the distance between the hooks can be adjusted is limited by the user's ability to quickly tighten or loosen the winged nut, thus limiting the ability to quickly apply or release the device in case of an emergency.

Thus, there remains a need for a lever that provides adequate rotation of a bone, for example, the femur, requires a small incision for insertion into the patient, provides precise adjustment of the force applied to the bone, and may be quickly applied and removed from the bone.

SUMMARY OF THE INVENTION

The present invention is directed to a lever for grasping bone tissue. The lever includes a shaft defining a channel, a claw member disposed on an end of the shaft for holding the bone tissue, and a rod threadably received in the channel. Rotation of the rod with respect to the shaft also causes the rod to move substantially axially with respect to the shaft to selectively position the distal end of the rod with respect to the claw member. The channel may include a first threaded portion and the rod may include a second threaded portion for threadably engaging the first threaded portion. The lever may include a bone engaging tip disposed on the distal end of the rod, which tip may be pointed, substantially concave, pivotable, or any other configuration known to one of ordinary skill in the art. The claw member may include a pair of spaced apart talons for grasping the bone tissue. The lever may further include an adjustment knob disposed on the rod. Additionally, a handle may be disposed on an end of the shaft.

According to another embodiment of the invention, the lever includes a locking member defining a second channel substantially aligned with the first channel. The locking member is moveable between a first position wherein the rod is axially slidable in the first channel, and a second position wherein the rod is substantially prevented from axial sliding in the first channel. When the locking member is in the second position, the locking member threadably engages the rod such that rotation of the rod with respect to the shaft causes the rod to move substantially axially with respect to the shaft. The locking member may include a first threaded portion, the rod may include a second threaded portion, and the locking member may be resiliently biased toward the rod such that the first threaded portion engages the second threaded portion. Alternatively, the locking member may be rotatable with respect to the rod between the first and second positions such that when the locking member is in the first position the first threaded portion is disengaged from the second threaded portion, and when the locking member is in the second position the first threaded portion engages the second threaded portion.

According to yet another embodiment of the present invention, the lever includes a handle portion and the claw member is removably and replaceably associated with the handle portion. The handle portion may include a shaft, and the claw member may be removably and replaceably associated with an end of the shaft. Alternatively, the claw member may include a shaft, and an end of the shaft may be removably and replaceably associated with the handle portion. The lever may further include a set of claw members, each of the claw members having different properties.

The present invention is further directed to a method of using the lever to align first and second portions of a fractured bone. The method includes the steps of inserting at least a portion of the lever into an incision near the fractured bone, positioning the claw member around the first portion of the fractured bone, positioning the rod to engage the bone first portion between the rod and the claw member, and maneuvering the bone lever to align the first portion of the bone with the second portion of the bone. The method may also include the step of rotating the rod.

BRIEF DESCRIPTION OF THE DRAWINGS

The detailed description will be better understood in conjunction with the accompanying drawings, wherein like reference characters represent like elements, as follows:

FIG. 9 is a side view of the femur lever of FIG. 5 with portions shown in phantom;

FIG. 10 is a top view of the femur lever of FIG. 5;

FIG. 11 is a cross-sectional view of the femur lever, taken along line XI—XI of FIG. 9;

FIG. 12 is a perspective view of the femur lever of FIG. 5, including a second embodiment of a quick-release button;

FIG. 13 is a cross-sectional view of the femur lever of FIG. 12;

FIG. 21 is a perspective view of a set of interchangeable claws for the femur lever of FIG. 17;

FIG. 22 is a side view of the set of interchangeable claws of FIG. 21;

DETAILED DESCRIPTION OF THE PREFERRED EMBODIMENTS

Figure 1:
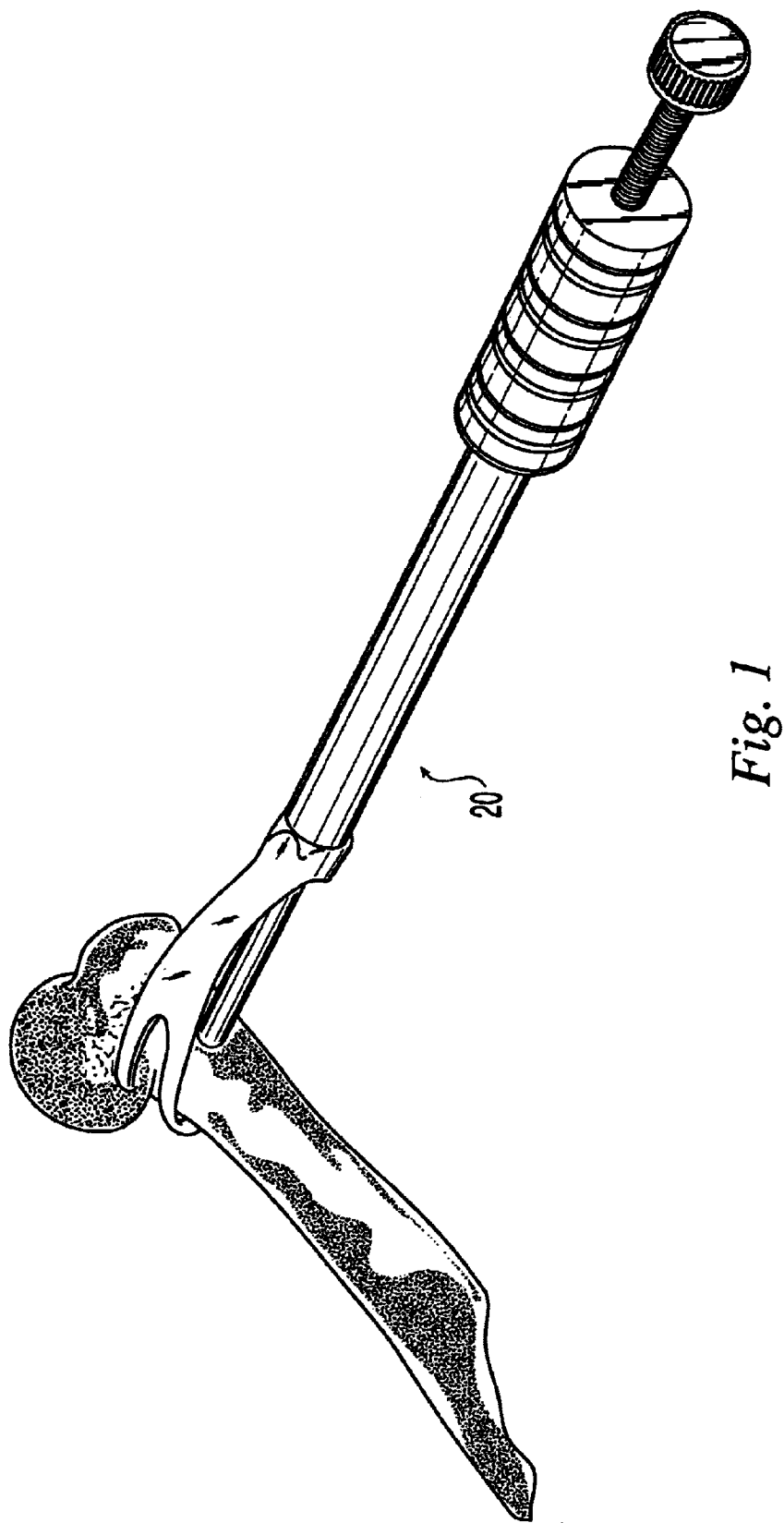
FIG. 1 is a perspective view of a femur lever according to the present invention, shown grasping a fractured femur.

Referring to FIG. 1, a femur lever 20 according to the present invention is shown grasping a portion of a fractured femur. Lever 20 is designed to pass through a percutaneous longitudinal incision in the area near the greater trochanter and grasp the proximal fragment of the fractured femur. Due to the streamlined configuration of the lever 20, the required incision is typically only four to six centimeters long and just deep enough to reach the area of the lessor trochanter, across the anterior aspect of the femur. Once inserted in the incision, the lever 20 can be manipulated to position and align the fractured fragments, for example, to align the medullary canal in preparation for intramedullary nailing. The present invention, however, is not to be limited to use with the femur, and may be used to manipulate and align any of the bones in the human and/or animal bodies.

Figure 2:
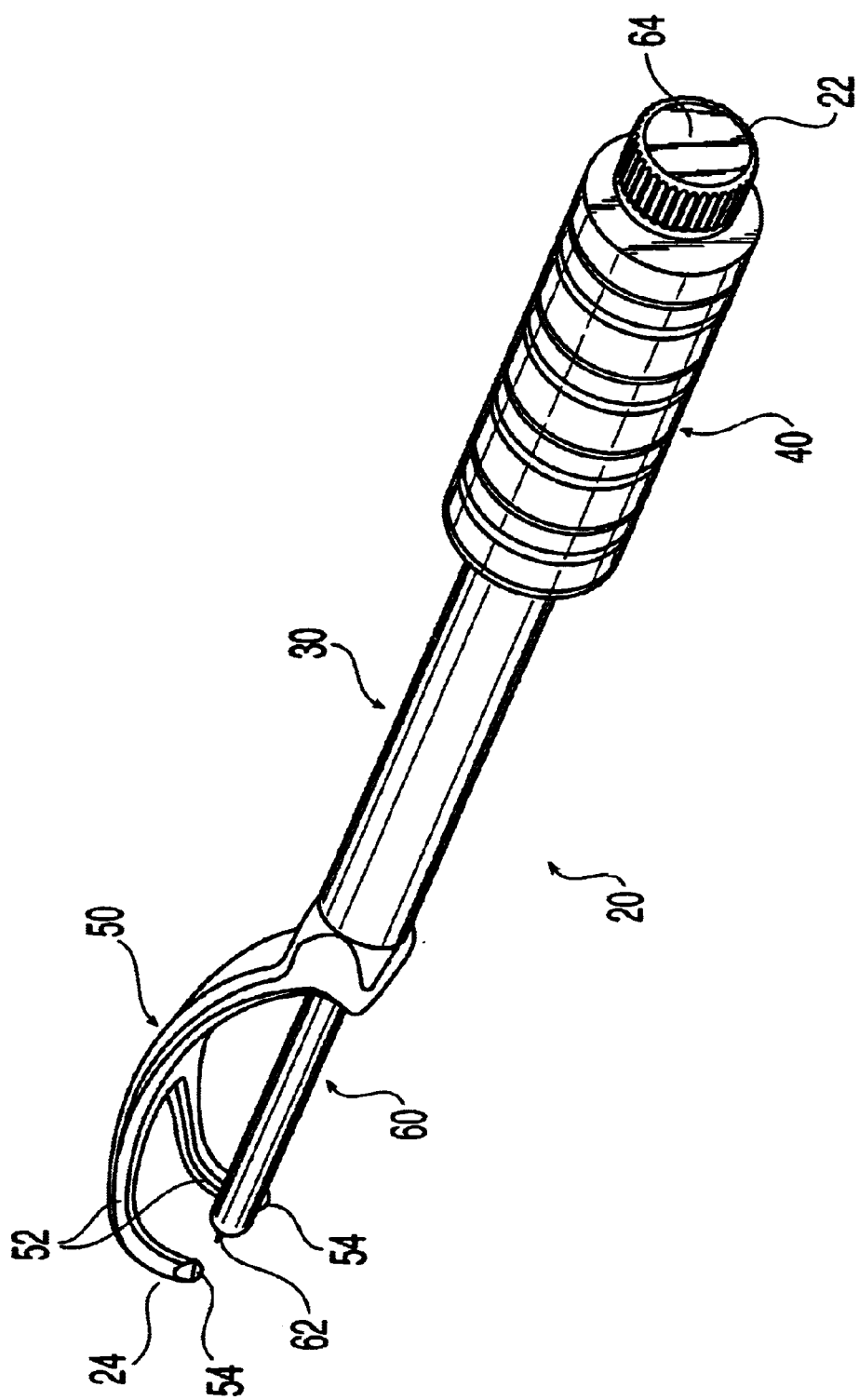
FIG. 2 is a perspective view of a first embodiment of the femur lever of FIG. 1.
Figure 3:
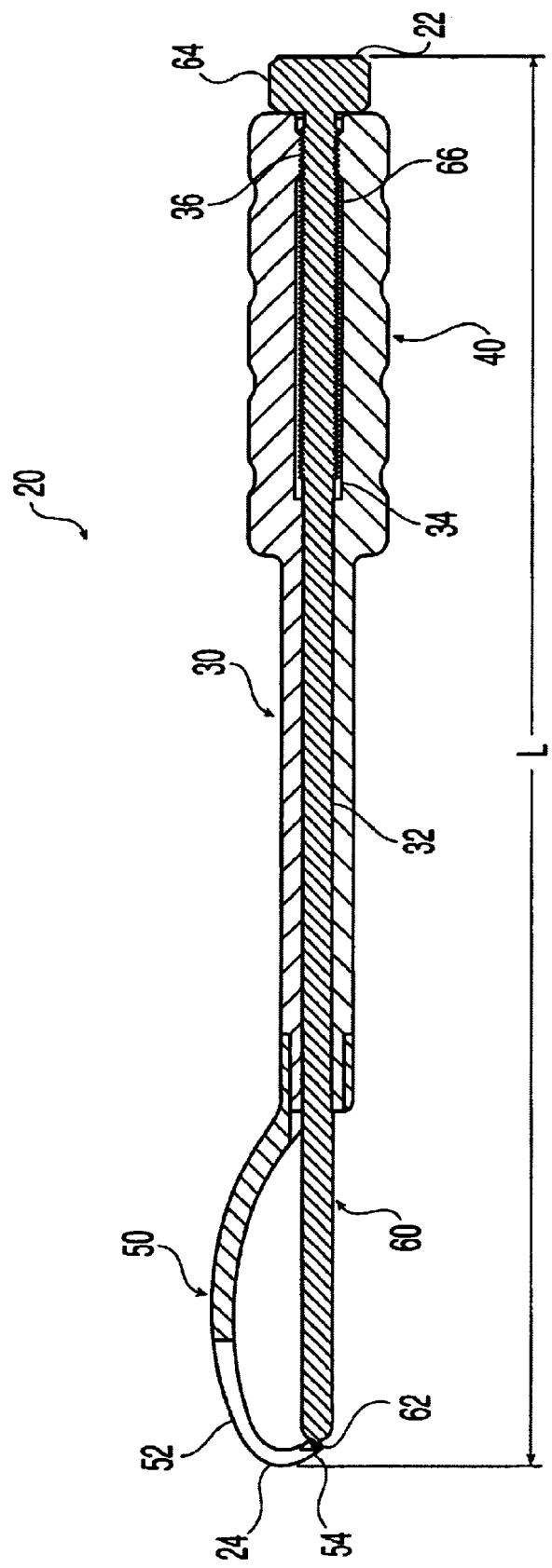
FIG. 3 is a cross-sectional view of the femur lever of FIG. 2.

Referring to FIGS. 2 and 3, a first illustrative embodiment of a bone lever according to the present invention is shown as lever 20. Lever 20 has a proximal end 22 and a distal end 24. An elongated shaft 30 connects a handle 40, located at the proximal end 22, to a bone grappling claw 50, located at the distal end 24. Handle 40 is sized to fit comfortably in the user's hand and may be provided with grooves, ridges, bumps, serrations, or any other surface treatment to increase a user's grip thereon. While handle 40 is shown as being substantially cylindrical and oriented substantially coaxially with shaft 30, other configurations are within the scope of the present invention. For example, handle 40 may be shaped and contoured to match the anatomy of a human hand. Handle 40 may also be offset, angled, or curved with respect to shaft 30.

Claw 50 includes a pair of spaced apart talons 52 that are curved to wrap around and grasp the femur. Each talon 52 includes a pointed tip 54 that assists in inserting the claw 50 into the patient, and also increases grip on the femur. Claw 50 is not to be limited to the configuration shown, and may alternatively be, for example, offset or angled with respect to shaft 30. Shaft 30 is dimensioned such that an overall length L (shown in FIG. 3) of lever 20 is preferably between about 25 centimeters and about 50 centimeters, thus allowing lever 20 to act as a moment arm for imparting force to the femur. Shaft 30, handle 40 and claw 50 may be formed integrally, or may alternatively be formed separately and connected using various techniques known to one of ordinary skill in the art, such as, for example, welding, brazing, soldering, bonding, pinning, screwing or press fitting. In the case that these parts are formed separately, shaft 30 is preferably made of 300 series stainless steel, handle 40 is preferably made of 6061-T6 aluminum, and claw 50 is preferably made of 17-4 PH heat treated stainless steel, however, other suitable materials will be known to one of ordinary skill in the art.

Figure 4:
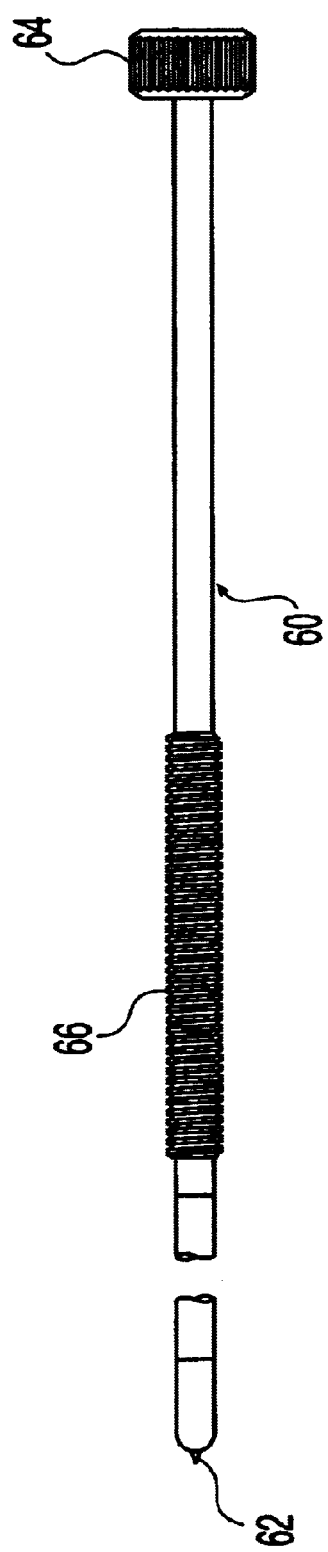
FIG. 4 is a top view of a first embodiment of a compression shaft of the femur lever of FIG. 2.

As shown in FIG. 3, shaft 30 and handle 40 define a channel 32 that may receive a compression rod 60. Compression rod 60, shown in FIG. 4, is an elongated rod that may include a bone engaging tip 62 at one end, and an adjustment knob 64 located proximate the handle 40. Bone engaging tip 62 is shown having a sharp point for engaging bone tissue, although other configurations as known by one of ordinary skill in the art are within the present invention. Adjustment knob 64 may be provided with grooves, ridges, bumps, serrations, or any other surface treatment to increase a user's grip thereon. Compression rod 60 further includes a threaded portion 66 that is received in an enlarged section 34 of channel 32. Threaded portion 66 is preferably a buttress screw thread, however, any type of thread known to one of ordinary skill in the art, such as an Acme thread or a Sharp-vee thread, may alternatively be used with the present invention. Compression rod 60 is preferably made of 17-4 PH heat treated stainless steel, however, other suitable materials as appropriate may alternatively be used.

Referring back to FIG. 3, enlarged portion 34 of channel 32 includes a threaded portion 36 that engages threaded portion 66 of compression rod 60 such that rotation of compression rod 60 moves compression rod 60 linearly with respect to channel 32, thereby moving bone engaging tip 62 toward or away from the tips 54 of talons 52. Thus, the distal end 24 of lever 20 may be inserted into an incision in the patient with the talons 52 oriented to grasp the anterior medial surface near the lesser trochanter, and adjustment knob 64 may be turned to advance the bone engaging tip 62 toward the area of the greater trochanter, thereby compressing and locking the fragment of the femur in claw 50 between the talons 54 and bone engaging tip 62. Adjustment knob 64 may subsequently be turned in the opposite direction to release the femur from claw 50.

Figure 5:
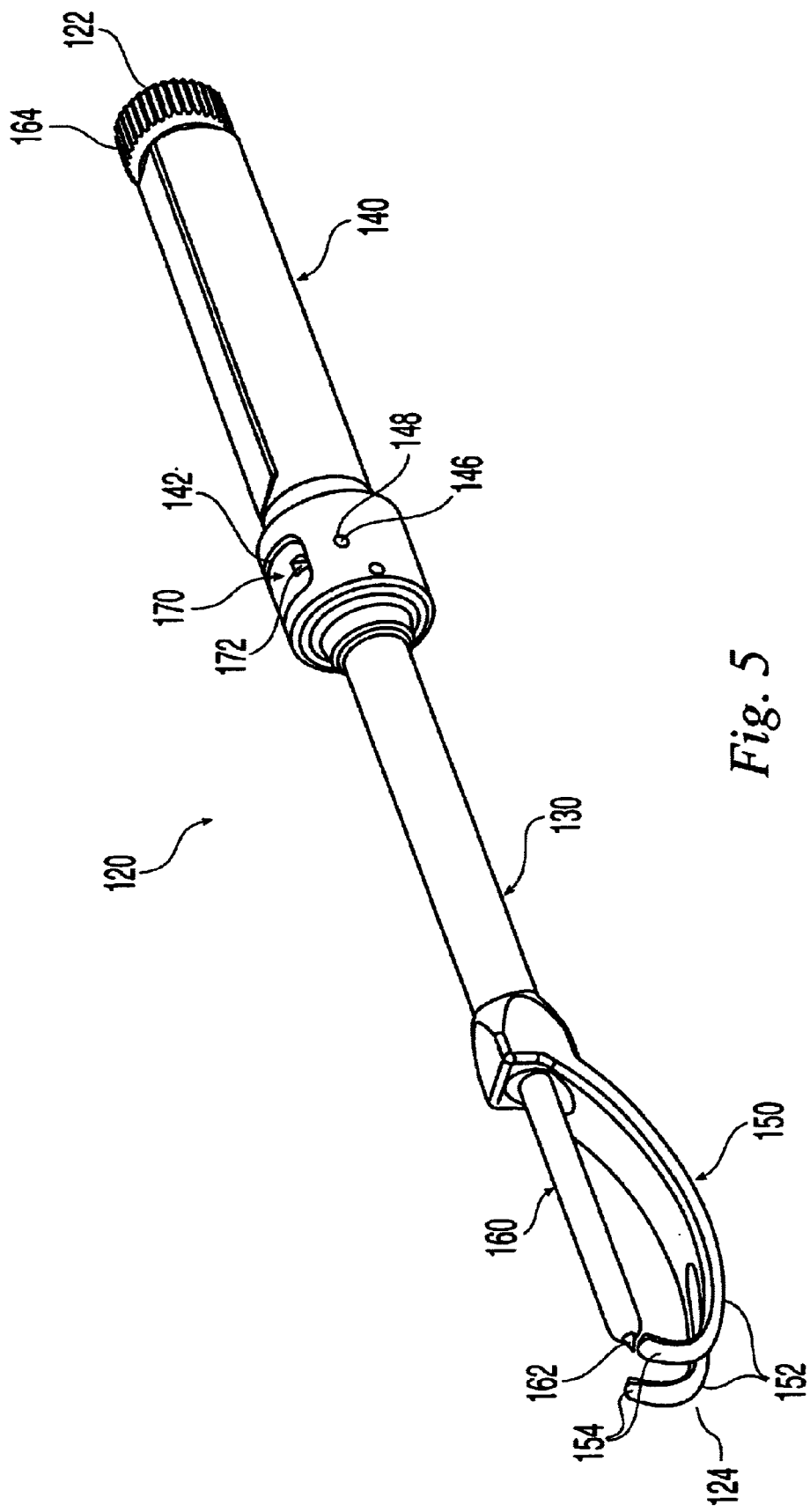
FIG. 5 is a perspective view of a second embodiment of a femur lever according to the present invention.

Referring to FIG. 5, a second illustrative embodiment of a femur lever is shown as lever 120. In addition to the features of lever 20, discussed above, lever 120 includes a quick-release button 170 for disengaging and re-engaging the threaded connection between compression rod 160 and channel 132 (not shown). Sufficiently depressing button 170 allows the user to freely slide compression rod 160 in channel 132, thereby allowing rapid advancement of bone engaging tip 162 toward or away from tips 154 of talons 152. The user might do this, for example, to rapidly position the bone engaging tip 162 of compression rod 160 in contact with the fractured fragment of the femur, or alternatively, to rapidly remove bone engaging tip 162 from contact with the fragment. Once button 170 is released, compression rod 160 is again threadably engaged in channel 132 (not shown), and adjustment knob 164 may be used to fine adjust the position of bone engaging tip 162.

Figure 7:
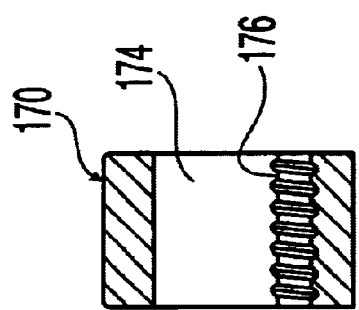
FIG. 7 is a cross-sectional view of the quick-release button, taken along line VII—VII of FIG. 8.
Figure 8:
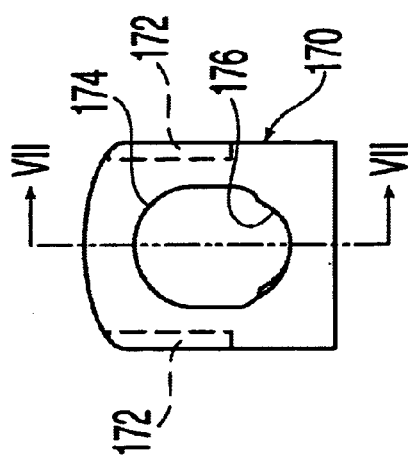
FIG. 8 is a front view of the quick-release button of FIG. 5.
Figure 6:
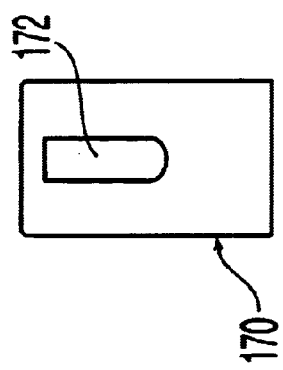
FIG. 6 is a side view of a first embodiment of a quick-release button of the femur lever of FIG. 5.

Referring to FIGS. 6–8, quick-release button 170 is shown, for example, as generally rectangular in shape and having a pair of keyways 172 formed in opposing sides thereof. A partially-threaded aperture 174 (shown in FIGS. 7 and 8) is formed through button 170 and defines an elongated, almost circular cross-section substantially the same size as a cross-section of channel 132. It will be readily appreciated, however the present invention is not to be limited to the cross-sectional geometry of aperture 174 shown and described. Aperture 174 includes a threaded portion 176 that corresponds to threaded portion 166 of compression rod 160 (not shown). Button 170 is preferably made of 304 series stainless steel, however, other suitable materials as suitable may be used.

Figure 18:
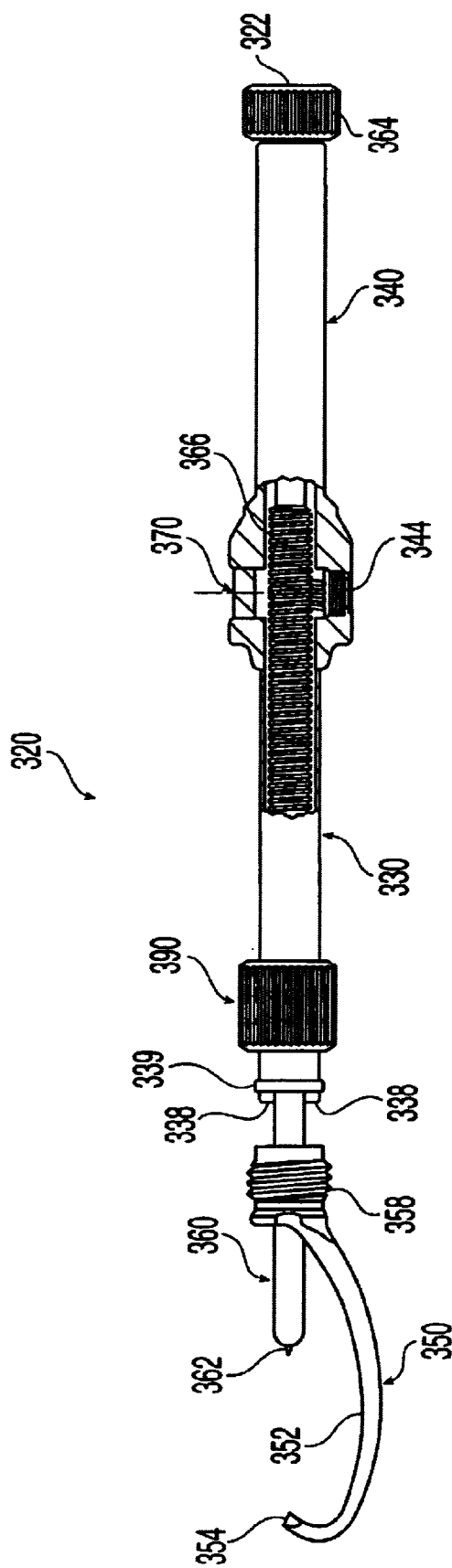
FIG. 18 is a partially-exploded side view of the femur lever, with portions shown in cross-section.

As shown in FIGS. 9–11, button 170 is slidably received in slot 142, formed in handle 140, with compression rod 160 passing though partially-threaded aperture 174. A pair of resilient members 144, shown as springs in FIG. 11, bias button 170 in direction D1, towards the opening in slot 142, such that threaded portion 176 engages threaded portion 166 of compression rod 160. Alternatively, as shown in FIG. 18, one resilient member 344 may be used instead of two, however, any type, number and configuration of resilient members may be used with the present invention to bias button 170 in direction D1. A pair of pins 146 preferably extend through apertures 148 in handle 140 and into keyways 172, to retain button 170 in slot 142. Pins 146 are not required, however, and button 170 may alternatively be retained in slot 142 solely by compression rod 160 passing through partially-threaded aperture 174. When button 170 is depressed in direction D2 against the force of springs 144, threaded portion 176 disengages threaded portion 166 and permits compression rod 160 to slide freely in channel 132. Releasing button 170 returns threaded portion 166 and 176 to threaded engagement and prevents compression rod 160 from sliding freely in channel 132.

Figure 16:
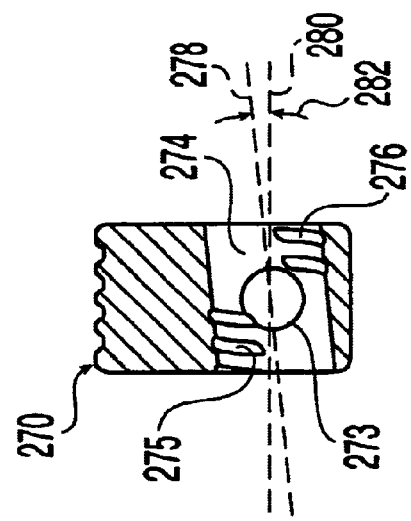
FIG. 16 is a cross-sectional view of the quick-release button, taken along line XVI—XVI of FIG. 15.
Figure 15:
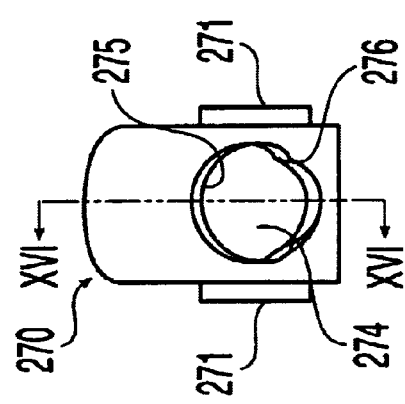
FIG. 15 is a front view of the quick-release button of FIG. 12.
Figure 14:
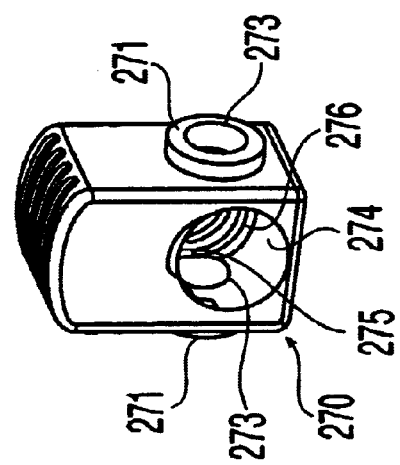
FIG. 14 is a perspective view of the quick-release button of FIG. 12.

Referring to FIGS. 12–16, a second embodiment of a quick release button is shown as button 270. As shown in FIGS. 14–16, button 270 is shown, for example, as generally rectangular and includes a pair of opposing bosses 271 (shown in FIGS. 14 and 15) formed thereon. A through hole 273 is formed through button 270 and is aligned through both of the bosses 271. A partially-threaded aperture 274 is also formed in button 270, which has a slightly larger diameter than compression rod 260 (shown in FIG. 13) and includes upper and lower threaded portions 275, 276. As shown in FIG. 16, partially-threaded aperture 274 defines a longitudinal axis 278 that is angularly disposed with respect to horizontal axis 280 of button 270 by an angle 282. Angle 282 is preferably about ten degrees, however, other angles may also be suitable as may be readily determined by one of ordinary skill in the art.

As shown in FIGS. 12 and 13, button 270 is disposed in slot 242, formed in handle 240, with compression rod 260 passing though partially-threaded aperture 274 (shown in FIG. 13). A pair of dowel pins 246, shown in FIG. 12, extend through elongated apertures 248 in handle 240 and into opposite ends of through hole 273 in button 270. Button 270 is thus retained in slot 242 and may rotate about dowel pins 246. Because the elongated apertures 248 are elongated with respect to the longitudinal axis of lever 220, button 270 may also slide in slot 242 along this longitudinal axis. Referring now to FIG. 13, because partially-threaded aperture 274 has a slightly larger diameter than compression rod 260, button 270 may rotate through an angle corresponding to angle 282 with respect to dowel pins 246 between an engaged and a non-engaged position. In the engaged position, shown in FIG. 13, the upper and lower threaded portions 275, 276 of partially-threaded aperture 274 are in threaded engagement with threaded portion 266 of compression rod 260. In the non-engaged position (not shown), however, upper and lower threaded portions 275, 276 are rotated out of threaded engagement with threaded portion 266, and compression rod 260 is free to slide in channel 232. Thus, the user may rotate button 270 to the non-engaged position to provide for rapid advancement of compression rod 260 and bone engaging tip 262 toward or away from tips 254 of claw 250, or alternatively, rotate button 270 to the engaged position and rotate adjustment knob 262 to fine tune the position of bone engaging tip 262.

Figure 17:
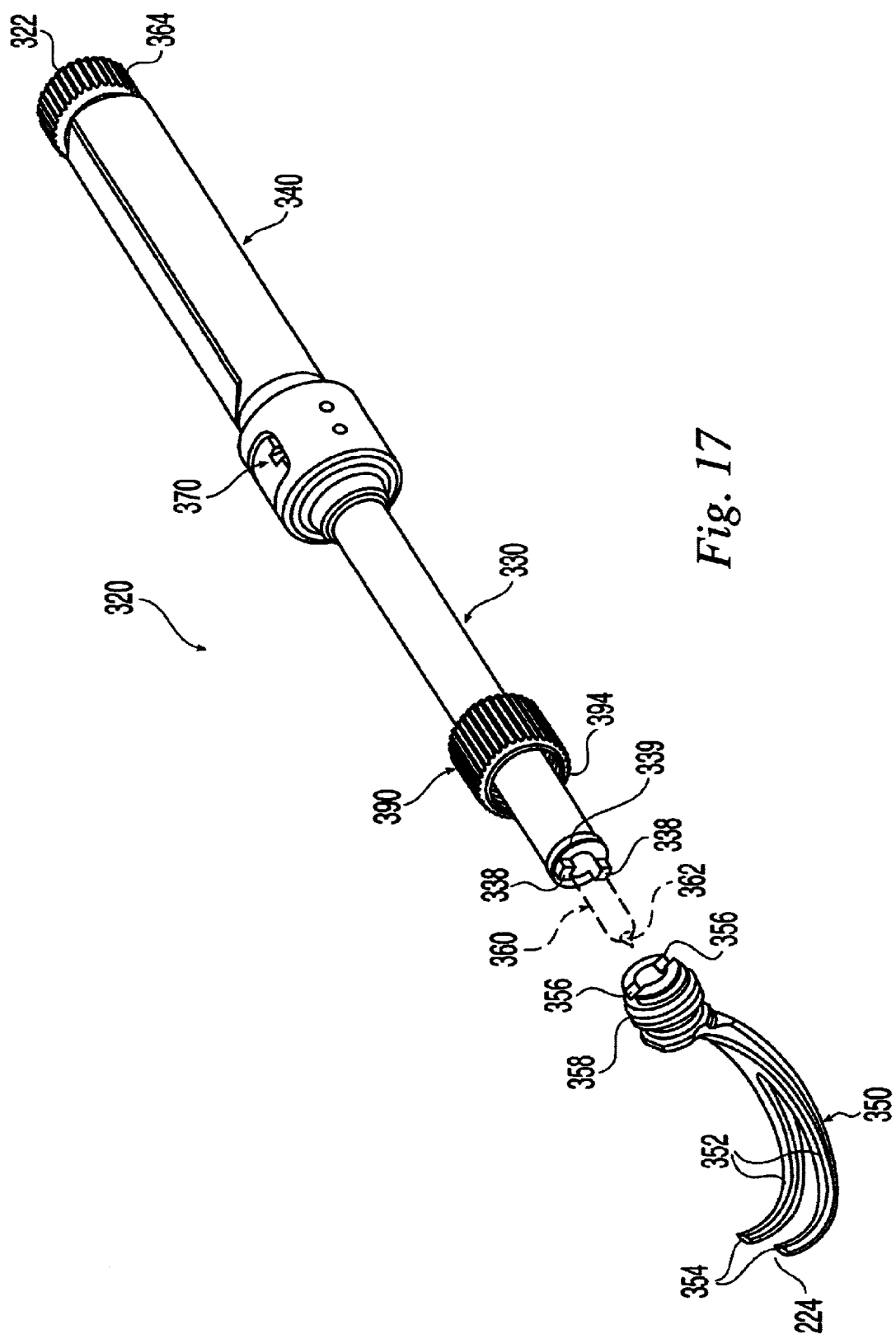
FIG. 17 is a partially-exploded perspective view of a third embodiment of a femur lever according to the present invention.
Figure 17A:
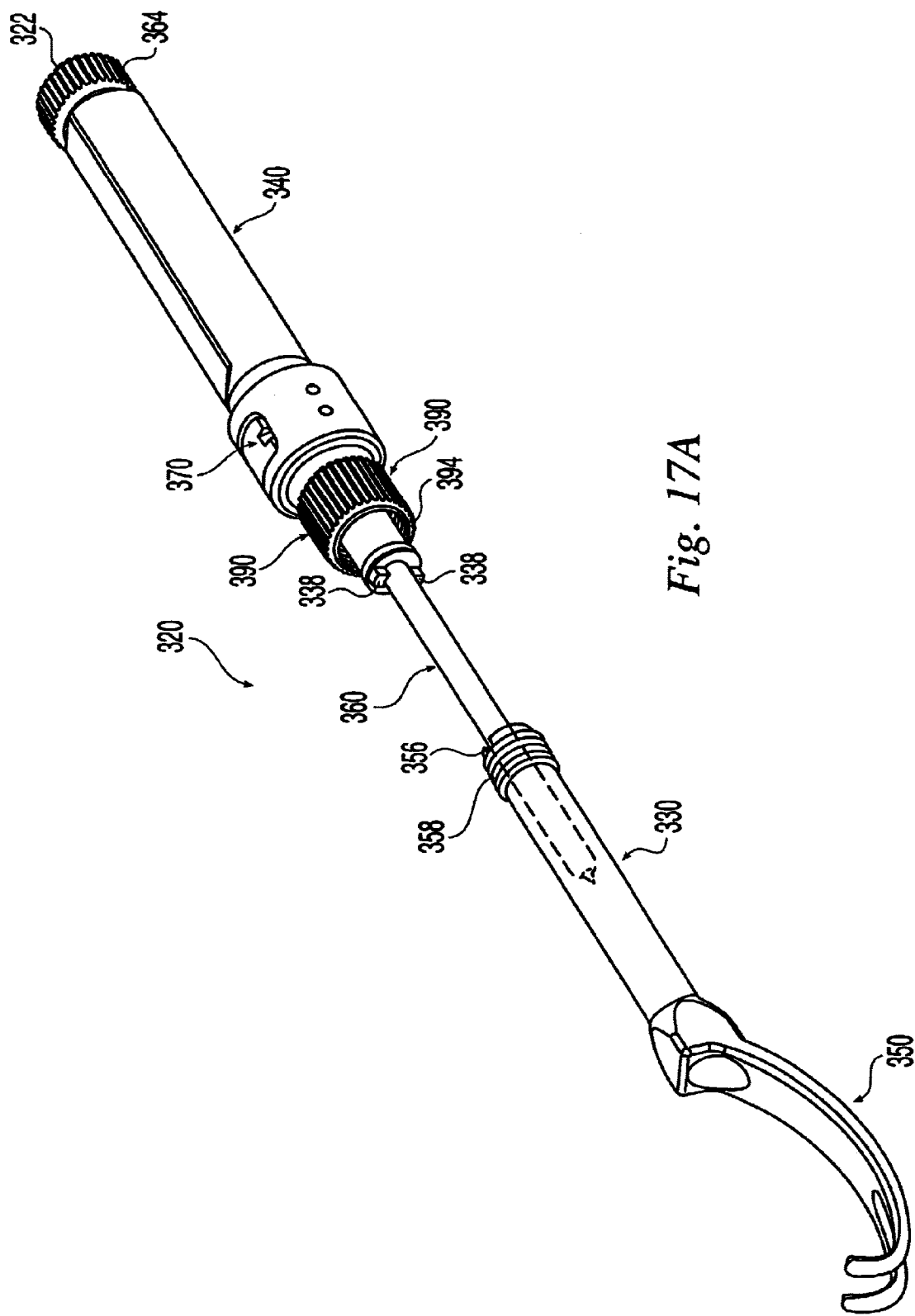
FIG. 17A is a partially-exploded perspective view of a variation of the femur lever of FIG. 17.
Figure 20:
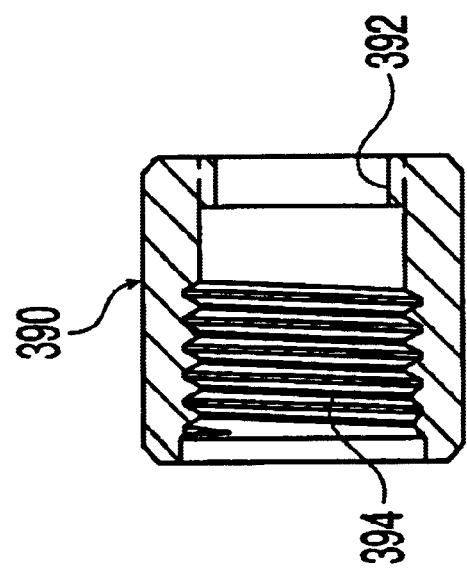
FIG. 20 is a cross-sectional view of the retaining nut of FIG. 19.
Figure 19:
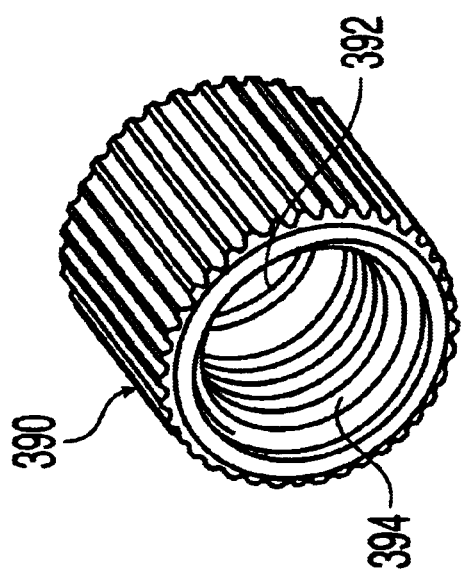
FIG. 19 is a perspective view of a retaining nut of FIG. 17.

Referring to FIGS. 17 and 18, a third illustrative embodiment of a femur lever is shown as lever 320. Lever 320 is similar to the levers discussed above except that claw 350 is removably and replaceably associated with handle 340. In the embodiment shown in FIG. 17, claw 350 may be removed from, and replaced on, the end of shaft 330 by way of retaining nut 390. Claw 350 has a keyway 356 formed therein that receives a pair of extensions 338 formed on the end of shaft 330. Keyway 356 and extensions 338 cooperate to align and prevent rotation of claw 350 with respect to handle 340. Retaining nut 390 slides on shaft 330 and has a preferably has a reduced portion 392 (shown in FIGS. 20 and 21) that catches on a shoulder 339 formed on the end of shaft 330 and prevents retaining nut 390 from sliding off the end of shaft 330. Retaining nut 390 also has a threaded portion 394 formed on its inside surface that matches a threaded portion 358 formed on claw 350. Alternatively, the configuration of retaining nut 390 and threaded portion 358 may be switched. When claw 350 is aligned with the end of shaft 330 with extensions 338 received in keyway 356, retaining nut 390 may be threaded onto the threaded portion 358 of claw 350 to lock claw 350 to shaft 330. To remove claw 350 from the end of shaft 330, for example to replace it with a different claw, the user simply has to turn retaining nut 390 sufficiently to disengage the threaded portions 358, 394. The present invention is not to be limited to the location of the removable connection of claw 350 shown in FIG. 17. For example, as shown in FIG. 17A, claw 350 and shaft 330 may be joined together and removably associated with handle 340. Thus, one of ordinary skill in the are will know and appreciate that claw 350 and/or shaft 330 may be removably associated with handle 340 at any number and combination of locations on lever 320. In addition, the present invention is not to be limited to the above-described structure for removing and replacing claw 350 and/or shaft 330 on handle 340, and various structures such as cams or quick-release pins may alternatively be used.

Referring to FIGS. 21 and 22, a set of six different claws 350*a–f* is shown, each claw having a different shape intended for a specific application. Claws 350*a* and 350*c* each have a pair of spaced apart talons 352 with sharply pointed tips 354. Claw 350*c*, however, has a narrower width Wc than claw 350*a*, and is therefore less invasive than claw 350*a*. Claws 350*b* and 350*e* each have a single broad blade 352 with a serrated tip 354. Once again, claw 350*d* has a width Wd that is narrower than the width Wb of claw 350*b*, and is therefore less invasive than claw 350*b*. Claw 350*e* has a pair of relatively long, narrow talons 352*e* with sharply pointed tips 354*e*, and claw 350*f* has a single long, narrow talon 350*f* with a sharply pointed tip 354*f*. The present invention is not to be limited to the shape and configurations of claw 350 shown, and many other configurations maybe suitable. For example, claw 350 may have three or more spaced apart talons. Claw 350 is preferably be made from 17-4 PH heat treated stainless steel, however, other suitable materials may be used. The above-described claws may be provided in a set with each claw having different properties, such as geometry, materials, etc.

Figure 23:
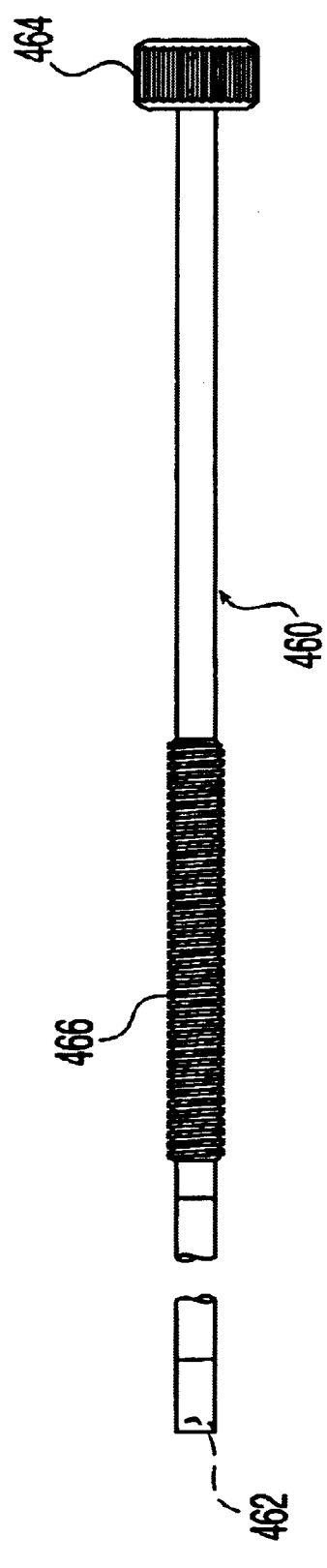
FIG. 23 is a side view of a second embodiment of a compression shaft according to the present invention.
Figure 24:
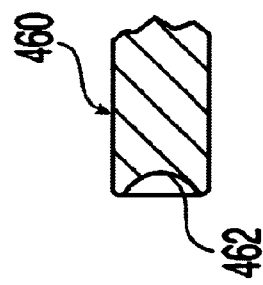
FIG. 24 is a enlarged detail view of a bone engaging tip of the compression shaft of FIG. 23.

Referring to FIGS. 23 and 24, a second embodiment of the compression shaft is shown. According to this embodiment of compression shaft 460, bone engaging tip 462 is substantially concave or cup-shaped to be optimally suited for use with osteoporotic bone, which is usually soft and spongy. Bone engaging tip 462 resolves itself into the bone and forms a secure grip thereon.

Figure 25:
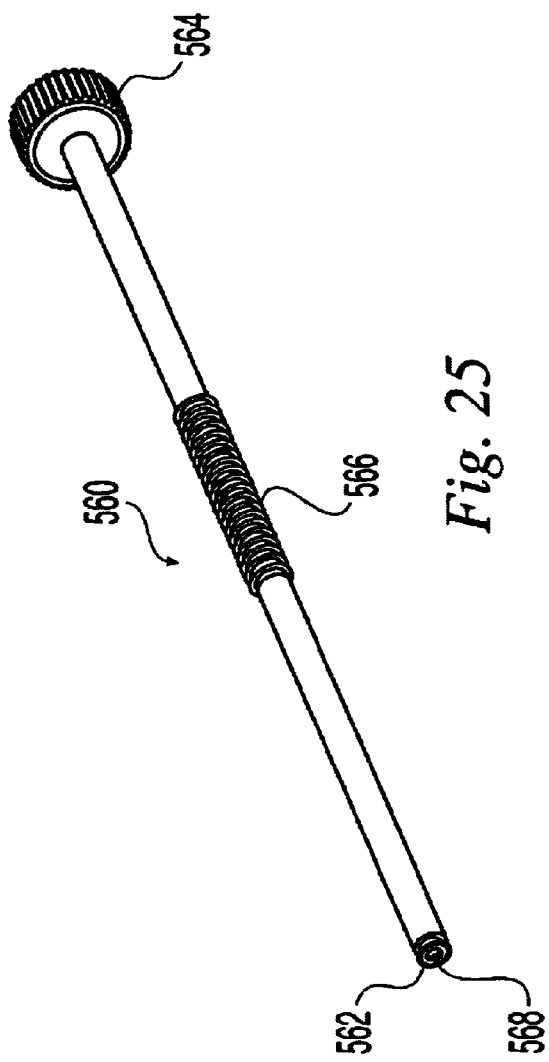
FIG. 25 is a perspective view of a third embodiment of a compression shaft having a pivotable bone engaging tip, according to the present invention.
Figure 26:
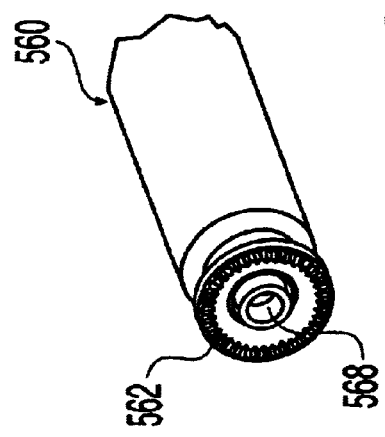
FIG. 26 is an enlarged detail view of the bone engaging tip of FIG. 25.
Figure 27:
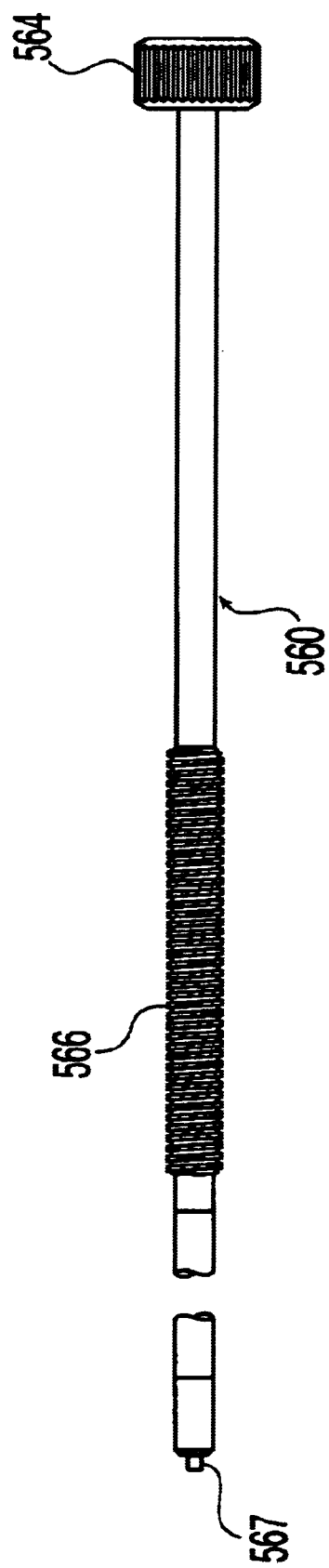
FIG. 27 is a side view of the compression shaft of FIG. 25, with the pivotable bone engaging tip removed.
Figure 28:
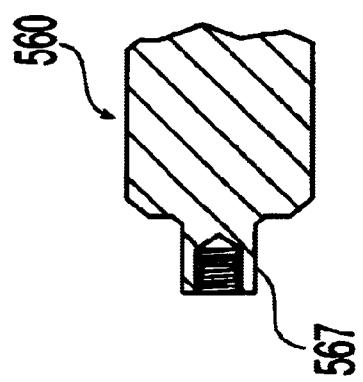
FIG. 28 is a enlarged cross-sectional view of an end of the compression shaft of FIG. 27.
Figure 29:
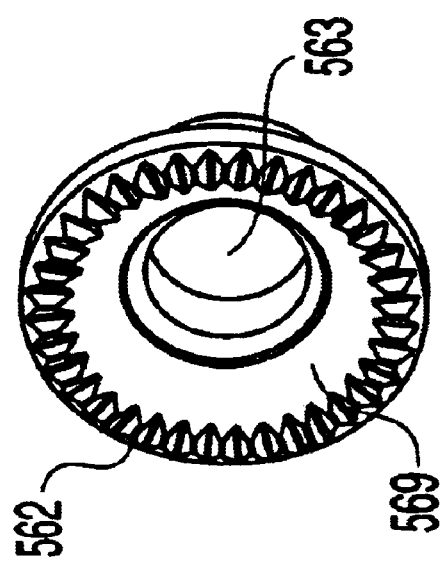
FIG. 29 is a perspective view of the pivotable bone engaging tip of FIG. 25.

Referring to FIGS. 25 and 26, a third embodiment of the compression shaft is shown. Compression shaft 560 includes a pivotable bone engaging tip 562 that is suited for use with osteoporotic bone. Pivotable tip 562 defines a central bore 563 (shown in FIG. 29) that slides over a threaded boss 567 (shown in FIGS. 27 and 28) formed on the end of shaft 530. Central bore 563 is slightly oversized with respect to threaded boss 567 to allow pivotable tip 562 to pivot thereon. A fastener 568, such as a machine screw, may be threaded into threaded boss 567 to retain pivotable tip 562 on the end of shaft 560. Pivotable tip 562 may alternatively be pivotally mounted to the end of shaft 560 using various other structures such as, for example, a ball joint. As shown in FIG. 29, pivotable tip has a slightly concave bone-contacting surface 569 that is provided with a surface treatment, such as serrations or teeth, that may dig into the bone and increase the frictional engagement between the tip 562 and the bone. The surface treatment is preferably in a stargrind pattern, as shown, however any number of configurations known to one of ordinary skill in the art may be suitable as well. All of the compression shafts described above may be used interchangeably with a femur lever as shown and described, thus permitting a single lever to be used with bones of different types and conditions.

While various descriptions of the present invention are described above, it should be understood that the various features described can be used singly or in any combination thereof. Therefore, this invention is not to be limited to only the specifically preferred embodiments depicted herein and is further not limited to use with the femur.

Further, it should be understood that variations and modifications within the spirit and scope of the invention may occur to those skilled in the art to which the invention pertains. Accordingly, all modifications attainable by one versed in the art from the disclosure set forth herein are to be included as further embodiments of the present invention. The scope of the present invention is accordingly defined as set forth in the appended claims.

What is claimed:

1. A lever for grasping bone tissue comprising:
   a shaft having a proximal end and a distal end, and defining a channel having a first threaded portion;
   a claw member disposed on the distal end of the shaft for holding the bone tissue;
   a rod having a proximal end, a distal end having a bone engaging tip, and a second threaded portion, the rod received in the channel; and
   a pivotable member associated with the bone engaging tip;
   wherein rotation of the rod with respect to the shaft causes the rod to move substantially axially with respect to the shaft to selectively position the bone engaging tip with respect to the claw member.

2. The lever of claim 1, wherein the bone engaging tip is pointed.

3. The lever of claim 1, wherein the bone engaging tip is substantially concave.

4. The lever of claim 1, wherein the claw member includes a pair of spaced apart talons.

5. The lever of claim 1, further comprising an adjustment knob disposed on the proximal end of the rod.

6. The lever of claim 1, further comprising a handle disposed on the proximal end of the shaft, wherein the handle is oriented substantially coaxially to the shaft.

7. A lever for grasping bone tissue, comprising:
   a shaft having a proximal end and a distal end, and defining a first channel;
   a claw member disposed on the distal end of the shaft for holding the bone tissue;
   a locking member defining a second channel substantially aligned with the first channel; and
   a rod at least partially received in the first and second channels for engaging the bone tissue;
   wherein the locking member is moveable between a first position wherein the rod is axially slidable in the first channel, and a second position wherein the rod is substantially prevented from axial sliding in the first channel.

8. The lever of claim 7, wherein when the locking member is in the second position, rotation of the rod with respect to the shaft causes the rod to move substantially axially with respect to the shaft.

9. The lever of claim 7, wherein:
   the locking member includes a first threaded portion; and
   the rod includes a second threaded portion;
   wherein when the locking member is in the first position, the first threaded portion is substantially disengaged from the second threaded portion, and when the locking member is in the second position, the first threaded portion engages the second threaded portion.

10. The lever of claim 7, wherein the locking member is resiliently biased toward the second position.

11. The lever of claim 7, wherein the locking member is rotatable with respect to the rod between the first and second positions.

12. The lever of claim 11, wherein the locking member defines a horizontal axis, and the second channel defines a longitudinal axis that is angularly disposed with respect to the horizontal axis.

13. The lever of claim 11, wherein the locking member is received in a slot in the shaft, and the slot is dimensioned to permit rotation of the locking member between the first and second positions.

14. A lever for grasping bone tissue comprising:
   a shaft having a proximal end and a distal end, and defining a first channel;
   a claw member disposed on the distal end of the shaft for holding the bone tissue;
   a rod received in the first channel for engaging the bone tissue; and
   a locking member operatively associated with the shaft and moveable between a first position wherein the rod is axially slidable in the first channel, and a second position wherein the locking member threadably engages the rod to substantially prevent axial sliding of the rod in the first channel.

15. The lever of claim 14, wherein when the locking member is in the second position, rotation of the rod with respect to the shaft causes the rod to move substantially axially with respect to the shaft.

16. The lever of claim 14, wherein the locking member defines a second channel, and the rod is at least partially received in the second channel.

17. The lever of claim 14, wherein:
   the locking member includes a first threaded portion;
   the rod includes a second threaded portion; and
   the locking member is resiliently biased into the second position such that the first threaded portion engages the second threaded portion.

18. The lever of claim 14, wherein:
   the locking member includes a first threaded portion;
   the rod includes a second threaded portion; and
   the locking member is rotatable with respect to the rod between the first and second positions;
   wherein when the locking member is in the first position the first threaded portion is disengaged from the second threaded portion, and when the locking member is in the second position the first threaded portion engages the second threaded portion.

19. A lever for grasping bone tissue comprising:
   a handle portion;
   a claw member for holding the bone tissue, the claw member removably and replaceably associated with the handle portion in an axial direction to allow the claw member to be removed from the handle portion and replaced with a different claw member in the axial direction; and
   a rod moveable with respect to the handle portion and having a bone engaging tip.

20. The lever of claim 19, wherein the handle portion further includes a shaft, and the claw member is removably and replaceably associated with an end of the shaft.

21. The lever of claim 19, wherein the claw member further includes a shaft, and an end of the shaft is removably and replaceably associated with the handle portion.

22. The lever of claim 19, further comprising:
   a retaining nut operatively associated with one of the handle portion and the claw member; and
   a threaded portion formed on the other of the claw member and the handle portion, wherein the retaining nut is threadable onto the threaded portion to retain the claw member on the handle portion.

23. The lever of claim 22, wherein the claw member and the handle portion are keyed to prevent rotation between the claw member and the handle portion.

24. The lever of claim 22, further comprising a shoulder formed on the handle portion or the claw member to prevent the retaining nut from sliding off of the handle portion or the claw member.

25. The lever of claim 19, further comprising a set of claw members, each of the claw members having different properties.

26. A method of aligning first and second portions of a fractured bone comprising the steps of:
   inserting at least a portion of the lever of claim 1 into an incision near the fractured bone;
   positioning the claw member around the first portion of the fractured bone;
   positioning the rod to engage the bone first portion between the distal end of the rod and the claw member; and
   maneuvering the bone lever to align the first portion of the bone with the second portion of the bone.

27. The method of claim 26, wherein positioning the rod further comprises rotating the rod.

28. The method of claim 26, wherein the fractured bone is a femur bone, and the first portion is a proximal portion.

29. A lever for grasping bone tissue comprising:
   a shaft having a proximal end and a distal end, and defining a channel having a first threaded portion;
   a claw member disposed on the distal end of the shaft for holding the bone tissue;
   a unitary rod having a proximal end, a distal end having an integral bone engaging portion, and a second threaded portion normally engaged with the first threaded portion, the rod received in the channel; and
   a locking member moveable to selectively disengage the first and second threaded portions;
   wherein when the first and second threaded portions are engaged, rotation of the rod with respect to the shaft causes the rod to move substantially axially with respect to the shaft to selectively position the bone engaging portion with respect to the claw member.

30. The lever of claim 29, further comprising a handle disposed on the proximal end of the shaft, wherein the handle is oriented substantially coaxially to the shaft.

31. The lever of claim 29, wherein the claw member is adapted and configured to be removably and replaceably associated with the distal end of the shaft.

32. The lever of claim 29, wherein the locking member is associated with the first threaded portion of the channel, the locking member being moveable between a first position wherein the first threaded portion is disengaged from the second threaded portion, and a second position wherein the first threaded portion is engaged with the second threaded portion.

33. The lever of claim 32, wherein the rod is axially slidable in the channel when the locking member is in the first position.

34. The lever of claim 29, wherein the bone engaging portion is a bone engaging tip.

35. A lever for grasping and manipulating bone tissue comprising:
   a shaft having a proximal end and a distal end, and defining a channel having a first threaded portion;

a claw member having two spaced apart talons for grasping and manipulating the bone tissue, the claw disposed on the distal end of the shaft; and a rod having a proximal end, a distal end having a bone engaging tip, and a second threaded portion, the rod received in the channel;

wherein when the claw is disposed about the bone tissue, rotation of the rod with respect to the shaft causes the rod to advance toward the bone tissue such that the bone engaging tip presses the bone tissue between the bone engaging tip and the spaced apart talons.

36. The lever of claim 35, wherein the bone engaging tip is pointed.

37. The lever of claim 35, wherein the bone engaging tip is substantially concave.

38. The lever of claim 35, further comprising a pivotable member associated with the bone engaging tip.

39. The lever of claim 35, further comprising an adjustment knob disposed on the proximal end of the rod.

40. The lever of claim 35, further comprising a handle disposed on the proximal end of the shaft, the handle being movable by a user to manipulate the bone tissue.

41. The lever of claim 35, wherein the bone engaging tip is substantially aligned with a mid-point located between the two spaced apart talons.

42. The lever of claim 35, wherein the claw is permanently attached to the distal end of the shaft.

* * * * *